(12) United States Patent
Takagi et al.

(10) Patent No.: US 7,833,399 B2
(45) Date of Patent: Nov. 16, 2010

(54) CONCENTRATION METHOD OF FINE PARTICLE DISPERSION AND CONCENTRATION APPARATUS OF FINE PARTICLE DISPERSION

(75) Inventors: Seiichi Takagi, Minamiashigara (JP); Tetsuo Ohta, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 1300 days.

(21) Appl. No.: 11/178,326

(22) Filed: Jul. 12, 2005

(65) Prior Publication Data

US 2006/0169589 A1 Aug. 3, 2006

(30) Foreign Application Priority Data

Jan. 28, 2005 (JP) ............................. 2005-022012

(51) Int. Cl.
*G01N 27/447* (2006.01)

(52) U.S. Cl. ........................................ 204/451; 204/601
(58) Field of Classification Search ......... 204/450–455, 204/600–605, 547, 643
See application file for complete search history.

(56) References Cited

U.S. PATENT DOCUMENTS

| | | | | |
|---|---|---|---|---|
| 5,081,017 A | * | 1/1992 | Longoria | ....................... 435/30 |
| 5,409,544 A | * | 4/1995 | Ota et al. | ................. 134/22.14 |
| 5,489,506 A | * | 2/1996 | Crane | ............................. 435/2 |
| 5,503,723 A | * | 4/1996 | Ruddy et al. | ................. 204/450 |
| 5,593,565 A | * | 1/1997 | Ajdari et al. | ................. 204/643 |
| 5,616,342 A | * | 4/1997 | Lyons | ......................... 424/450 |
| 5,653,859 A | * | 8/1997 | Parton et al. | ................. 204/450 |
| 6,221,654 B1 | * | 4/2001 | Quake et al. | ............. 435/287.3 |
| 6,964,736 B2 | * | 11/2005 | Quake et al. | ................. 204/452 |
| 6,969,454 B2 | * | 11/2005 | Bryning et al. | ............. 204/601 |
| 7,211,442 B2 | * | 5/2007 | Gilbert et al. | ............... 436/177 |
| 2004/0067547 A1 | * | 4/2004 | Harbron et al. | ............... 435/34 |

FOREIGN PATENT DOCUMENTS

JP A 9-304338 11/1997

OTHER PUBLICATIONS

N201, "Development of a Continuous Particle Separation Method by Using the Microchannel Laminar Flow System," Preprints of 69th Annual Meeting by Society of Chemical Engineers, pp. 1-5, conference held Apr. 2-4, 2004.
N202, "Study of Particle Behavior in Micro-Separator/Classifier Using Euler-Lagrange Method," Preprints of 69th Annual Meeting by Society of Chemical Engineers, pp. 5-9, conference held Apr. 2-4, 2004.

* cited by examiner

*Primary Examiner*—Alex Noguerola
(74) *Attorney, Agent, or Firm*—Oliff & Berridge, PLC (57) ABSTRACT

The present invention provides a concentration method of a fine particle dispersion containing fine particles to be electrophoretically migrated, for concentrating the fine particle dispersion by allowing the fine particle dispersion to flow in a laminar flow in a channel having a micro-width to which an electric field is applied in a direction intersecting the direction of a fine particle dispersion flow. The invention also provides a concentration apparatus of a fine particle dispersion using the concentration method.

9 Claims, 4 Drawing Sheets

CONCENTRATION METHOD OF FINE PARTICLE DISPERSION AND CONCENTRATION APPARATUS OF FINE PARTICLE DISPERSION

This application claims priority under 35 USC 119 from Japanese Patent application No. 2005-022012, disclosure of which is incorporated by reference herein.

BACKGROUND OF THE INVENTION

1. Field of the Invention

The present invention relates to a concentration method of a fine particle dispersion using a micro-flow channel and a concentration apparatus of a fine particle dispersion comprising a micro-flow channel.

2. Description of the Related Art

In business fields handling fine particles, specially, food product production, production of fine particle products such as pigments and polymers, sludge treatment as environmental protection technology, fine particle dispersions are delivered and fine particles are collected in the form of slurries or solid state. Particularly, if a fine particle dispersion has a low concentration, the transportation efficiency is low and therefore, it is required to concentrate such a dispersion. As concentration methods commonly used, methods of centrifugal separation utilizing sedimentation, filtration, drying and evaporation, and classification are used, however, basically these methods are carried out in a batch manner and accordingly, the methods require not only many steps, but also the recovery efficiency is low. Further, normally, the methods require a high energy and a long processing time. As a method of transporting, adhering and recovering fine particles in a fine particle dispersion, there is a method of utilizing electrophoresis. For example, a method in which silica fine particles are dispersed in an aqueous alkaline solution, are negatively charged by applying an electric field between the polishing tool and a counter electrode, is used, so that the particles are adhered to a polishing tool to improve specular polishing. However, this method has an extremely poor efficiency and requires a long time and a high energy.

On the other hand, methods of carrying out chemical reactions and unit operation in micro regions have been investigated in recent years. In relation to this, methods and apparatuses of extraction, separation, mixing and particle formation focusing on a short diffusion time have been proposed. Among these methods, as a method in which electrophoresis is applied to a micro device, a method of transporting an extremely small amount of a sample by applying an electric field in a similar manner to a capillary electrophoresis chip by which an electric field is applied to a sample in a micro flow channel and the sample is electrophoretically migrated by the electric field for detection by a photo-detector is proposed (e.g. Japanese Patent Application Laid-Open (JP-A) No. 9-304338). However, the method is used for transporting an extremely small biochemical substance such as a protein or DNA and is not used for transporting fine particles, and cannot be applied to concentration of a fine particle dispersion.

As described, there is no method or apparatus made available for concentrating a fine particle dispersion continuously in a low number of steps, at a high recovery efficiency, and low energy without any problems.

SUMMARY OF THE INVENTION

The present invention aims to provide a concentration method of a fine particle dispersion containing fine particles to be electrophoretically migrated for concentrating the dispersion at a low energy and high efficiency, and high fine particle recovery efficiency in a short period of time, and to provide a compact type and space-saving concentration apparatus of a fine particle dispersion containing fine particles to be delectrophoretically migrated for concentrating the dispersion at low energy and high efficiency and high fine particle recovery efficiency in a short time.

As a result of intensive investigations, the inventors of the invention have found that the above-mentioned problems can be solved by applying an electric field in a direction intersecting the flowing direction of a fine particle dispersion in a laminar flow; thereby moving the fine particles in the vicinity of one wall surface to recover the fine particles therefrom; so that a concentrated fine particle dispersion is obtained and consequently the present invention has been accomplished.

The first aspect of the invention is to provide a concentration method of a fine particle dispersion containing fine particles to be electrophoretically migrated, for concentrating the fine particle dispersion by making the fine particle dispersion to flow in a laminar flow to a channel having a micro-width wherein an electric field is applied in a direction intersecting the flowing direction of a fine particle dispersion.

The second aspect of the invention is to provide the concentration method of a fine particle dispersion of the first aspect, wherein the channel having a micro-width for making the fine particle dispersion to flow has an angle in the range of 0 to 45° with respect to the gravity direction or the buoyant direction.

The third aspect of the invention is to provide the concentration method of a fine particle dispersion of the first aspect, wherein the channel having a micro-width has a width of 50 to 1,000 μm.

The fourth aspect of the invention is to provide the concentration method of a fine particle dispersion of the first aspect, wherein the electric field is applied to the channel at an angle in the range of 30 to 150° with respect to the direction of the fine particle dispersion flow in a fine particle transporting part.

The fifth aspect of the invention is to provide the concentration method of a fine particle dispersion of the first aspect, wherein the flow rate of the fine particle dispersion in a liquid delivering section is in the range of 0.001 to 100 ml/hr.

The sixth aspect of the invention is to provide the concentration method of a fine particle dispersion of the first aspect, wherein the fine particles to be electrophoretically migrated have absolute value of zeta potential in the range of 1 to 1,000 mV.

The seventh aspect of the invention is to provide the concentration method of a fine particle dispersion of the first aspect, wherein the fine particles have a volume average particle diameter in the range of 0.1 μm to 500 μm.

The eighth aspect of the invention is to provide the concentration method of a fine particle dispersion of the first aspect, wherein a liquid medium in the fine particle dispersion has a conductivity in the range of 0 to 50 μs/cm.

The ninth aspect of the invention is to provide the concentration method of a fine particle dispersion of the first aspect, wherein the difference calculated by subtracting the specific gravity of a liquid medium in the fine particle dispersion from the specific gravity of the fine particles is in the range of −0.9 to 20.

The tenth aspect of the invention is to provide the concentration method of a fine particle dispersion of the first aspect, wherein the concentration of the fine particles in the fine particle dispersion is in the range of 0.1 to 40% by volume.

The eleventh aspect of the invention is to provide a concentration apparatus of concentrating a fine particle dispersion containing fine particles to be electrophoretically migrated, comprising a channel having a micro-width, and an electrode for applying an electric field in the direction to the channel intersecting the channel having a micro-width, wherein the channel having a micro-width comprises an introduction section for introducing the fine particle dispersion at one end thereof, a liquid transporting section for transporting the fine particle dispersion introduced through the introduction section toward the other end in a laminar flow, a fine particle delivering section positioned in the downstream side of the transporting section and delivering fine particles of the fine particle dispersion to one direction side of the electric field by applying the electric field, a recovery section for recovering the fine particle dispersion where the fine particles are delivered, and a discharge section for discharging a liquid other than the fine particle dispersion recovered in the recovery section.

The twelfth aspect of the invention is to provide the concentration apparatus of a fine particle dispersion of the eleventh aspect, wherein the channel with a micro-width for making the fine particle dispersion to flow has an angle in the range of 0 to 45° with respect to the gravity direction or the buoyant direction.

The thirteenth aspect of the invention is to provide the concentration apparatus of a fine particle dispersion of the eleventh aspect, wherein the channel having a micro-width has a width of 50 to 1,000 μm.

The fourteenth aspect of the invention is to provide the concentration apparatus of a fine particle dispersion of the eleventh aspect, wherein the electric field is applied to the channel at an angle in the range of 30 to 150° with respect to the direction of the fine particle dispersion flow in a fine particle transporting section.

The fifteenth aspect of the invention is to provide the concentration apparatus of a fine particle dispersion of the eleventh aspect, wherein the channel having a micro-width has a cross-sectional shape in the direction perpendicular to the flow direction is a rectangular shape.

The sixteenth aspect of the invention is to provide the concentration apparatus of a fine particle dispersion of the eleventh aspect, wherein the fine particles to be electrophoretically migrated have absolute value of zeta potential in the range of 1 to 1,000 mV.

The seventeenth aspect of the invention is to provide the concentration apparatus of a fine particle dispersion of the eleventh aspect, wherein the fine particles have a volume average particle diameter in the range of 0.1 μm to 500 μm.

DETAILED DESCRIPTION OF THE INVENTION

A concentration method of a fine particle dispersion of the present invention is a concentration method of a fine particle dispersion for concentrating a fine particle dispersion containing fine particles to be electrophoretically migrated, wherein the fine particle dispersion is concentrated by allowing the fine particle dispersion to flow in a laminar flow in a channel having a micro-width to which an electric field is applied in the direction intersecting the flow direction.

In the invention, the fine particles to be electrophoretically migrated are fine particles having zeta potential. The channel having micro-width means a channel having a size of the maximum width of 5,000 μm or smaller in cross-section of the channel. In the channel having a micro-width of the invention, a microreactor having a channel having a width of several to several thousand μm may be used preferably as the channel with a micro-width. The width of the microreactor is preferably 50 to 1,000 μm and more preferably 50 to 500 μm. Here, the term "width" refers to a length of one side of the cross-section of the channel, when the channel has a rectangular shape.

The microreactor used in the present invention is a reactor having multiple flow paths (channels) having dimensions in micrometers. Since the channels of the microreactor have dimensions in micrometers, both the dimensions of the channel and a flow rate are small, and the Reynolds number of the channels is 2300 or less. Thus, the reactor having the channel having dimensions in micrometers is a device in which a laminar flow is predominant, rather than an ordinary reactor in which a turbulent flow is predominant.

The Reynolds number (Re) is represented by the equation: $Re = uL/\upsilon$, wherein u represents the flow rate, L represents the characteristic length, and $\upsilon$ represents the kinematic viscosity coefficient. When this value is about 2300 or less, a laminar flow is predominant.

As described above, in the field where the laminar flow is dominant, since the viscosity factor greatly affects on the flow as compared with an inertia factor, the flow becomes a flow where the medium is not substantially moved to the direction intersecting the flow direction. Accordingly, the diffusion of particles due to a turbulent current can be prevented and the concentration can be carried out efficiently.

An electric field is applied to the channel having a micro-width to be employed for the concentration method of the fine particle dispersion of the invention in the direction intersecting the flow direction. When an electric field is applied, the fine particles in the fine particle dispersion flowing in the electric field are moved to one direction of the electric field and a concentrated fine particle dispersion can be obtained by recovering the fine particle dispersion at the side where the fine particles are moved in the channel having a micro-width.

The concentration method of the fine particle dispersion of the invention can be carried out using a concentration apparatus of the fine particle dispersion of the invention as described below.

The concentration apparatus of the fine particle dispersion of the invention is a concentration apparatus of a fine particle dispersion containing fine particles to be electrophoretically migrated and comprises a channel a micro-width, an electrode for applying an electric field in the direction intersecting the channel having a micro-width, wherein the channel having a micro-width comprises an introduction section for introducing the fine particle dispersion at one end of the channel, a transporting section for transporting the fine particle dispersion introduced through the introduction section toward the other end of the channel in a laminar flow, a fine particle delivering section positioned at the downstream side of the transporting section and delivering the fine particles in the fine particle dispersion to one direction side of the electric field by applying the electric field, a recovery section for recovering the fine particle dispersion where the fine particles are delivered, and a discharge section for discharging a liquid other than the fine particle dispersion recovered in the recovery section.

Figure 1:
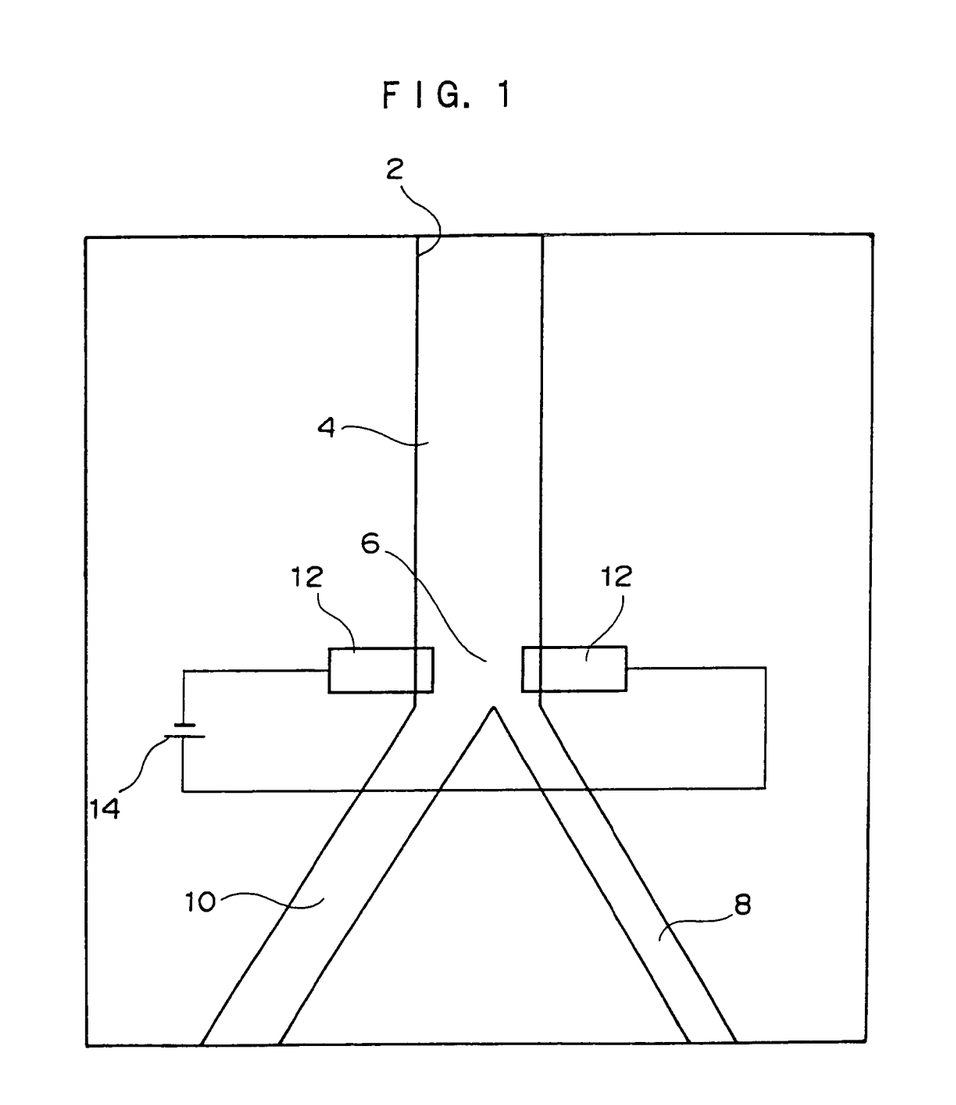
FIG. 1 is a schematic structural view showing one example of a concentration apparatus of a fine particle dispersion of the present invention.

One example of the concentration apparatus of the fine particle dispersion of the present invention will be described in accordance with FIG. 1. FIG. 1 is a schematic structural view showing one example of a concentration apparatus of a fine particle dispersion of the invention.

The concentration apparatus of the fine particles shown in FIG. 1 is a microreactor having a channel with a width of several μm to several thousand μm and comprises a channel having a micro-width having an introduction section 2 for introducing the fine particle dispersion in one end of the channel, a transporting section 4 for transporting the fine particle dispersion introduced through the introduction section 2 toward the other end of the channel in a laminar flow, a fine particle delivering section 6 positioned at the downstream side of the transporting section and delivering the fine particles of the fine particle dispersion to one direction side of an electric field by applying the electric field, a recovery section 8 for recovering the fine particle dispersion into which the fine particles dispersion at the side where the delivered fine particle dispersion have been delivered flows, and a discharge section 10 having a micro-wide channel for discharging a liquid other than the fine particle dispersion recovered in the recovery section, and an electrode 12 connected to an electric power source 14 for applying an electric field in the direction intersecting the channel having the micro-width.

The transporting section 4 refers to a region from the introduction section 2 to the fine particle delivering section 6, and the fine particle delivering section 6 refers to a region in the channel having a micro-width where the electric field is applied.

The electric field may be applied to the direction intersecting the flow direction of the fine particle dispersion and it is preferable for the electric field to be applied at an angle in the range of 30 to 150° relative to the direction of the fine particle dispersion flow in the fine particle delivering section 6, and more preferably at an angle rectangular to the fine particle delivering section 6. If the electric field is applied at an angle in the range of 30 to 150° with respect to the direction of the fine particle dispersion flow in the fine particle delivering section 6, the fine particles can efficiently be delivered.

In the concentration apparatus of the fine particle dispersion of the invention, a second transporting section may be formed between the fine particle delivering section 6 and the recovery section 8 and between the fine particle delivering section 6 and the discharge section 10. In such a case, the fine particle dispersion containing the fine particles which have been moved in the fine particle delivering section 6 flows into the recovery section 8 and the discharge section 10. However, it is preferable that the fine particle delivering section 6 directly communicates with the recovery section 8 and the discharge section 10 without the second transporting section and the like.

The recovery section 8 and discharge section 10 may be sufficient if fine particle dispersion at the side of the fine particles which have been moved in the fine particle delivering section 6 and liquids other than this dispersion can flow into the recovery section 8 and discharge section 10, respectively, and they are preferably branched two channels in accordance with the moving direction of the particles by the application of the electric field.

The cross-sectional view at the direction rectangular to the flow direction in the recovery section 8 and discharge section 10 may be set properly so as to recover the fine particle dispersion with a desired concentration.

The cross-sectional shape of the channel having a micro-width of the invention in the direction perpendicular to the flow direction is not particularly limited, however it is preferable to be a rectangular shape.

The concentration apparatus of the fine particle dispersion of the invention preferably includes a channel for transporting the fine particle dispersion in the channel having a micro-width having an angle in the range of 0 to 45° with respect to the gravity direction, more preferably in the range of 0 to 30°, even more preferably in the range of 0 to 15°, and even more specifically in the range of 0 to 10°, in the case that the specific gravity of the fine particles of the fine particle dispersion is higher than that of the medium liquid, which is disperse medium. If the angle exceeds 45° with respect to the gravity direction, the fine particles sediment and are deposited easily on the wall face of the flow channel, that may result in blocking of the channel in the case the specific gravity of the fine particles of the fine particle dispersion is higher than that of the medium liquid.

The angle of the channel having a micro-width with respect to the gravity direction means an angle of the center line of the respective channels with respect to the gravity direction In the case that the specific gravity of the fine particles of the fine particle dispersion is higher than that of the medium liquid, if the diameter of the channel having a micro-width or the cross-sectional shape in the direction rectangular to the flow direction varies with locations, the lower wall surface of the channel along the flow direction of the channel for transporting the fine particle dispersion has preferably an angle relative to the gravity direction in the range of 0 to 45°, more preferably in the range of 0 to 30°, even more preferably in the range of 0 to 15°, and even more specifically in the range of 0 to 10°.

Figure 2:
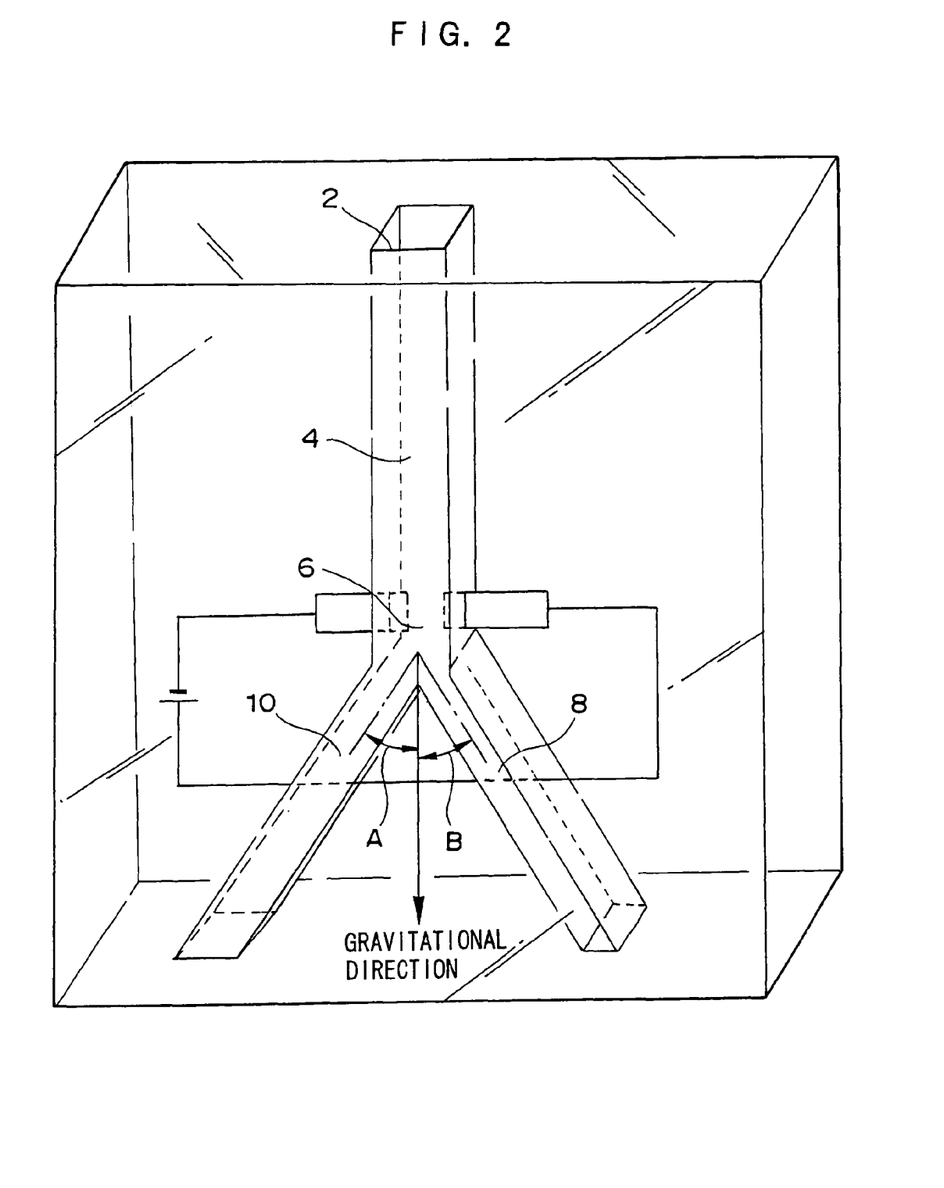
FIG. 2 is an explanatory drawing for explaining the direction of the installation of the concentration apparatus of a fine particle dispersion of the invention.

As described above, in an example of the concentration apparatus of the fine particle dispersion of the invention comprising the channel having a micro-width having an angle of the channel with respect to the gravity direction preferably in the range of 0 to 45°, as shown in FIG. 2, the apparatus comprises a transporting section 4 and a fine particle delivering section 6 arranged linearly along a straight line and a channel having a micro-width having a recovery section 8 and a discharge section 10 at an angle in a range 0 to 45° relative to the straight line are arranged such that an introduction section 2 of the channel is above with respect to the gravity direction and the transporting section 4 and the fine particle delivering section 6 are below with respect to the gravity direction.

In the concentration apparatus shown in FIG. 2, the channel from the introduction section 2 to the fine particle delivering section 6 has an angle of 0° with respect to the gravity direction, the recovery section 8 has an angle of A° with respect to the gravity direction and the discharge section 10 has an angle of B° with respect to the gravity direction.

On the other hand, in the case that the specific gravity of the fine particles in the fine particle dispersion is smaller than that of the medium liquid, which is a disperse medium, in the concentration apparatus of the fine particle dispersion of the invention, the channel for transporting the fine particle dispersion in the channel having a micro-width has preferably an angle in the range of 0 to 45° relative to the buoyant direction, more preferably in the range of 0 to 30°, even more preferably in the range of 0 to 15°, and even more preferably in the range of 0 to 10°. If the angle relative to the buoyant direction exceeds 45°, the fine particles float and tend to adhere to the inner wall face of the channel, resulting in blocking of the channel in some cases.

The angle of the channel having a micro-width relative to the buoyant direction refers to an angle of the center lines of the respective channels relative to the buoyant direction.

Further, in the case that the specific gravity of the fine particles in the fine particle dispersion is smaller than that of the medium liquid, if the diameter of the channel having a micro-width or the cross-sectional shape in the direction rectangular to the flow direction varies with locations, the upper wall surface of the cannel along the flow direction of the channel for transporting the fine particle dispersion has preferably an angle with respect to the gravity direction in the range of 0 to 45°, more preferably in the range of 0 to 30°, even more preferably in the range of 0 to 15°, and even more preferably in the range of 0 to 10°.

As described above, in an example of the concentration apparatus of the fine particle dispersion of the invention comprising the channel having a micro-width having an angle of the channel with respect to the buoyant direction preferably in the range of 0 to 45°, in contrast to the case that the specific gravity of the fine particles is higher than that of the medium liquid, the apparatus comprises a transporting section 4 and a fine particle delivering section 6 arranged linearly along a straight line are arranged such that an introduction section of a channel having a micro-width is below in the buoyant direction and a transporting section 4 and fine particle delivering section 6 are above in the buoyant direction, and a recovery section 8 and a discharge section 10 are above the fine particle delivering section 6.

As a material for a microreactor to be used for the concentration apparatus of the fine particle dispersion of the invention, commonly used materials such as metals, ceramics, plastics, and glass can be used and it is desirable to be appropriately selected in accordance with the medium liquid to be transported.

The concentration apparatus of the fine particle dispersion of the invention comprises an electrode for applying an electric field in direction intersecting the above-mentioned channel having a micro-width. The micro-device having an electrode for applying the electric field in direction intersecting the above-mentioned channel having a micro-width can be obtained by producing in such a manner that a micro-device, which does not have electrode, formed by a conventionally known method, and thereafter an electrode is applied thereto by vapor deposition or the like.

The concentration of the fine particle dispersion using the concentration apparatus of the fine particle dispersion of the invention is carried out first by introducing the fine particle dispersion to be concentrated into the introduction section 2. The introduction of the fine particle dispersion into the introduction section 2 is preferably carried out by the use of a microsyringe, a rotary pump, a screw pump, a centrifugal pump, and a piezoelectric pump with pressure.

The fine particle dispersion introduced through the introduction section 2 is transported toward the other end (downstream) of the channel, and when the dispersion reaches the fine particle delivering section 6, the fine particles are led to the downstream while being moved to one direction side of the electric field owing to the electric field applied in the direction intersecting the channel and arrive to a branched point where the transporting section branches into the recovery section 8 and the discharge section 10. Here, the fine particles are moved and the concentrated fine particle dispersion flows in the recovery section 8 to be recovered there. On the other hand, the liquid other than the concentrated fine particle dispersion flows in the discharge section 10 to be discharged.

The flow rate of the fine particle dispersion in the transporting section 4 is preferably 0.001 to 100 ml/hr and more preferably 0.01 to 50 ml/hr.

If the flow rate of the fine particle dispersion in the transporting section is lower than 0.001 ml/hr, the fine particles is susceptible to the inner fall of the channel and thus uniform flow may not be attained. On the other hand, if the flow rate of the fine particle dispersion in the transporting section exceeds 100 ml/hr, the movement of the fine particles to in one direction of the electric field may become incomplete.

Further, in the invention, the voltage to be applied to the electrode may vary with the type of the fine particle dispersions, it is preferably 0.5 to 5 V and more preferably 1 to 3 V. If the voltage exceeds 5 V, the medium liquid such as water is sometimes electrolyzed to form bubbles and becomes an obstacle, and if it is lower than 0.5 V, the movement of the fine particles in one direction of the electric field may become incomplete.

The fine particles in the fine particle dispersion to be employed in the invention can preferably be used if the fine particles are electrophoretically migrated. The fine particles to be electrophoretically migrates means the fine particles having zeta potential.

The zeta potential of the fine particles to be electrophoretically migrated can be measured by an apparatus which can commonly be used for measurement of the zeta potential. In the invention, Spectrometer DT1200 (manufactured by Dispersion Technology Corp.) is employed for the measurement. The fine particles to be used in the invention is preferable to have an absolute value of the zeta potential in the range of 1 to 1,000 mV in a dispersed state, and more preferably an absolute value of in the range of 30 to 300 mV in light of productivity.

The volume average particle diameter of the fine particles is preferably in the range of 0.1 μm to 500 μm and more preferably in the range of 0.1 μm to 200 μm. If the volume average particle diameter of the fine particles is smaller than 0.1 μm, the fine particles may not stably be moved in the electric field, and if it exceeds 500 μm, blockage of the channel may take place.

In the present invention, the volume-average particle size of the fine particles is a value measured with a Coulter counter TA-II model (manufactured by Beckman Coulter, Inc.) except when the fine particles have a particle size of 5 μm or less. The volume-average particle size is measured by use of an optimal aperture depending on the particle size level of the fine particles. However, in cases where the fine particles have a particle size of about 5 μm or less, the volume-average particle size is measured with a laser scattering particle size distribution measuring device (trade name: LA-920, manufactured by Horiba, Ltd.).

The specific gravity of the fine particles is measured with a pycnometer (trade name: Ultrapycnometer 1000, manufactured by Yuasa Ionics Co., Ltd.) by gas phase displacement method (pycnometer method).

The specific gravity of any liquid medium is measured with a specific gravity determination kit (trade name: AD-1653) manufactured by A & D Co., Ltd.

The shape of the fine particles used in the method for classifying fine particles of the present invention is not particularly limited. However, if the fine particles are of a needle form, and in particular if the long axis thereof is larger than ¼ of the width of the channel, the possibility that the channel clogs may become high. From this perspective, the ratio of the long axis length of the fine particles to the short axis length thereof (that is, the long axis length/the short axis length) is preferably from 1 to 50, and more preferably from 1 to 20. It is desired to select the channel width appropriately in accordance with the particle size and the particle shape.

The fine particles to be electrophoretically migrated for the invention have a positive or negative polarity in a medium liquid. For example, in a water-based medium, if the fine particles have molecular terminals of —COOH, —CN, and —SO$_3$ on the surface of the particles, they show a negative polarity, and if the fine particles have molecular terminals of —NH$_3$ and —NH$_4^+$ on the surface of the particles, they show a positive polarity.

Examples of the fine particles showing the negative polarity in the medium liquid may include, as anionic polymers, polymers of monomers having a hydroxyl group, a carboxyl group, a sulfonic acid group, a phosphoric acid group and an acid anhydride, e.g. polymerizable anionic monomers such as 2-acrylamido-2-methylpropanesulfonic acid, N-methylolacrylamide, methacrylic acid, acrylic acid, 2-hydroxyethyl methacrylate, 2-hydroxypropyl methacrylate, glycidyl methacrylate, polypropylene glycol monomethacrylate, polyethylene glycol monomethacrylate, tetrahydrofurfuryl methacrylate, acid phosphoxyethyl methacrylate, and maleic anhydride; and copolymers of these monomers with one or more monomers exemplified below. Examples of one or more monomers to compose the copolymers may include styrenes such as styrene, o-methylstyrene, p-methylstyrene, 2,4-dimethylstyrene, p-n-butylstyrene, p-tert-butylstyrene, p-n-dodecylstyrene, p-chlorostyrene, and p-phenylstyrene; vinylnaphthalenes; ethylenic unsaturated monoolefins such as ethylene, propylene, and isobutylene; vinyl esters such as vinyl chloride, vinyl acetate, vinyl butyrate, and vinyl benzoate; α-methylene aliphatic monocarboxylic acid esters such as methyl acrylate, ethyl acrylate, n-butyl acrylate, isobutyl acrylate, propyl acrylate, n-octyl acrylate, dodecyl acrylate, lauryl acrylate, 2-ethylhexyl acrylate, stearyl acrylate, 2-chlorethyl acrylate, phenyl acrylate, methyl α-chloroacrylate, methyl methacrylate, ethyl methacrylate, propyl methacrylate, n-butyl methacrylate, isobutyl methacrylate, n-octyl methacrylate, dodecyl methacrylate, lauryl methacrylate, 2-ethylhexyl methacrylate, stearyl methacrylate, phenyl methacrylate, dimethylaminoethyl methacrylate, and diethylaminoethyl methacrylate; acrylic acid or methacrylic acid derivatives such as acrylonitrile, methacrylonitrile, and acrylamide; vinyl ethers such as vinyl methyl ether, vinyl ethyl ether, and vinyl isobutyl ether; vinyl ketones such as vinyl methyl ketone, vinyl hexyl ketone, and methyl isopropenyl ketone; and N-vinyl compounds such as N-vinylpyrrole, N-vinyl carbazole, N-vinylindole, and N-vinylpyrrolidone. One or more of their polymers may be added to the polymerizable monomers. Among them, copolymers or blends of poly (acrylic acid), and polyacrylonitrile are preferable.

Examples of the fine particles showing positive pole in the medium liquid may include, for example, as cationic polymers, polymers of nitrogen-containing monomers such as dimethylaminoethyl methacrylate, dimethylaminoethyl acrylate, diethylaminoethyl methacrylate, diethylaminoethyl acrylate, N-n-butoxyacrylamide, trimethylammonium chloride, diacetoneacrylamide, acrylamide, N-vinylcarbazole, vinylpyridine, 2-vinylimidazole, 2-hydroxy-3-acryloxypropyltrimethylammonium chloride and their N-quaternization monomers; and copolymers of the above-mentioned nitrogen-containing monomers and one or more monomers exemplified below. The above-mentioned monomers for composing the copolymers are styrene and their derivatives such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; as vinyl monomers, e.g. ethylenic unsaturated monoolefins such as ethylene, propylene, butylene, and isobutylene; halogenated vinyl compounds such as vinyl chloride, vinylidene chloride, vinyl bromide, and vinyl fluoride; vinyl esters such as vinyl acetate, vinyl propionate vinyl benzoate, and vinyl butyrate; α-methylene aliphatic monocarboxylic acid esters such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, phenyl acrylate, and methyl α-chloroacrylate; vinyl ethers such as vinyl methyl ether, vinyl ethyl ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, N-vinylpyrrolidone; vinyl naphthalates; acrylic acid and methacrylic acid derivatives acrylonitrile, methacrylonitrile, and acrylamide. Among these polymers, copolymers or blends of poly(dimethylaminoethyl methacrylate) are preferable.

The fine particles to be used in the invention may include, as inorganic fine particles, metal oxides such as $SiO_2$ and $TiO_2$ showing a negative polarity, and aluminum oxide showing a positive polarity. Further, it has been known that these metal oxides treated with a silane treatment agent exhibit a negative or positive polarity in accordance with the types and the ratio of the terminal groups of the treatment agents. For example, $SiO_2$ treated with an amino group-containing silane treatment agent gives the positive polarity.

The polarity of the fine particles used in the invention varies with not only the surface property of the particles, but also with the type of ions dissolved liquid and the type of surfactants in the medium, and is basically controllable.

On the other hand, in the invention, in general, any medium liquid can be used and the conductivity of the medium liquid is preferably 0 to 50 μs/cm, more preferably 0 to 20 μs/cm, and even more preferably 0 to 10 μs/cm. If the conductivity of the medium liquid exceeds 50 μs/cm, the fine particles may not stably moved in the electric field.

As the medium liquid used preferably in the invention, for example, water and alcohol are usable, and specially, a water-based medium containing water as a main component thereof is preferable.

The difference calculated by subtracting the specific gravity of the medium liquid from the specific gravity of the fine particles is preferably in the range of −0.9 to 20, more preferably in the range of −0.6 to 11, and even more preferably in the range of −0.3 to 4. If the difference exceeds 20, the sedimentation of the fine particles in the medium liquid takes place considerably, that may result in problems such as blocking of the channel or the like. On the other hand, if the difference is lower than 0.9, the flotation of the fine particles becomes significant so that the concentration of the fine particles in the electric field may become insufficient.

In the invention, desirable combinations of the fine particles and the medium liquid are a combination of fine particles of polystyrene acryl type or polyester type compounds having a carboxyl group on the surface thereof and a water-based solvent, and combination of fine particles of polystyrene acryl type or polyester type fine particles having an amino group or a quaternary ammonium group on the surface thereof and a water-based solvent. Among them, the combination of fine particles of polystyrene acryl type resin having a carboxyl group on the surface and a water-based solvent is preferable.

The concentration of the fine particles in the fine particle dispersion of the invention is preferably in the range of 0.1 to 40% by volume and more preferably in the range of 1 to 25% by volume. If the concentration of the fine particles exceeds 40% by volume, the channel may possibly be clogged and if it is lower than 0.1% by volume, the recovery efficiency may possibly become insufficient.

EXAMPLES

Hereinafter, the present invention will be described more in detail with reference to Examples; however, the invention is not to be considered as being limited by the Examples.

Example 1

A fine resin particle dispersed liquid 1, a resin fine particle dispersion 2, a releasing agent fine particle dispersion, and a pigment dispersion are produced in advance by the following method.

—Preparation of a Fine Resin Particle Dispersion 1—

| Styrene | 370 parts |
|---|---|
| n-Butyl acrylate | 30 parts |
| Acrylic acid | 6 parts |
| Dodecanthiol | 24 parts |
| Carbon tetrabromide | 4 parts |

A solution of a mixed solution containing the above components, and a solution obtained by dissolving 6 parts of a nonionic surfactant (trade name: NONIPOL 400, manufactured by Sanyo Chemical Industries, Ltd.), and 10 parts of an anionic surfactant (trade name: NEOGEN R, manufactured by Dai-ichi Kogyo Seiyaku Co., Ltd.) in 550 parts of ion-exchanged water are placed in a flask, and emulsifying dispersed. While stirring slowly and mixing the emulsified dispersion for ten minutes. While stirring slowly and mixing the emulsified dispersion for ten minutes, 50 parts of ion-exchanged water in which 4 parts of ammonium persulfate is dissolved, is introduced into the flask. Thereafter, the flask is sufficiently filled with nitrogen, and the flask is heated in an oil bath so that the inside of the system is set to 70° C., and the emulsion polymerization is continuously carried out for 5 hours.

The volume average particle diameter of the fine resin particles of the latex obtained is measured by a laser diffraction scattering particle size distribution measuring apparatus (trade name: LA-700, manufactured by Horiba, Ltd.), and the volume average particle diameter is 160 nm. The weight average molecular weight (in terms of polystyrene) is measured using THF is used as a solvent by a molecular weight measuring instrument (trade name: HLC-8020, manufactured by Tosoh Corporation). The weight average molecular weight is 13200.

—Preparation of a Fine Resin Particle Dispersion 2—

| Styrene | 280 parts |
|---|---|
| n-Butyl acrylate | 120 parts |
| Acrylic acid | 8 parts |

A solution of a mixed solution containing the above components, and a solution obtained by dissolving 6 parts of a nonionic surfactant (trade name: NONIPOL 400, manufactured by Sanyo Chemical Industries, Ltd.), and 12 parts of an anionic surfactant (trade name: NEOGEN R, manufactured by Dai-ichi Kogyo Seiyaku Co., Ltd.) in 550 parts of ion-exchanged water are placed in a flask, and emulsifying dispersed. While stirring slowly and mixing the emulsified dispersion, 50 parts of ion-exchanged water in which 3 parts of ammonium persulfate is dissolved is introduced into the flask. Thereafter, the flask is sufficiently filled with nitrogen, and the flask is heated in an oil bath so that the inside of the system is set to 70° C., and the emulsion polymerization is continuously carried out for 5 hours.

The various characteristics of the latex obtained are measured in the same manner as the resin fine particle dispersion 1. The volume average particle diameter of the fine resin particles is 100 nm, and the weight average molecular weight is 540000.

—Releasing Agent Fine Particle Dispersed Liquid—

| Paraffin wax (trade name: HNPO190, manufactured by Nippon Seiro Co., Ltd., melting point: 85° C.) | 50 parts |
|---|---|
| Cationic surfactant (trade name: SANISOL B50, manufactured by Kao Corporation) | 5 parts |
| Ion-exchanged water | 200 parts |

The above components are mixed, and sufficiently dispersed by a homogenizer (trade name: ULTRATALAX T50 manufactured by IKA Corporation). while being heated at 95° C. The dispersion is transferred and further subjected to s dispersing treatment, and thereby a releasing agent fine particle dispersion in which a volume average particle diameter of the releasing agent fine particle is 540 nm is obtained.

—Preparation of a Pigment Dispersed Liquid—

| Carbon black (trade name: MOGAL L, manufactured by Cabot Corporation) | 50 parts |
|---|---|
| Nonionic surfactant (trade name: NONIPOL 400, manufactured by Sanyo Chemical Industries, Ltd.) | 5 parts |
| Ion-exchanged water | 200 parts |

The above components are mixed, and sufficiently dispersed by a homogenizer, (trade name: ULTRATALAX T50 manufactured by IKA Corporation) for 10 minutes. Thereby a pigment dispersion in which carbon black having a volume average particle diameter of 255 nm is dispersed is obtained.

—Preparation of an Aggregated Particle (Toner Particle) Dispersion—

| Resin fine particle dispersion 1 | 120 parts |
|---|---|
| Resin fine particle dispersion 2 | 80 parts |
| Releasing agent fine particle dispersion | 40 parts |
| Pigment dispersion | 30 parts |
| Cationic surface-active agent (trade name: Sanisol B50, manufactured by Kao Corporation) | 1.5 parts |

The above components are placed in a round-bottomed stainless steel flask, and are sufficiently mixed and dispersed by a homogenizer, (trade name: ULTRATALAX T50 manufactured by IKA Corporation). The flask is heated at 48° C. with stirring in an oil bath to heat to 48° C., and maintained at the same temperature for 30 minutes. Thereafter, the temperature of the oil bath is raised to 50° C., and maintained the same temperature for 1 hour to obtain aggregated particles. The volume average particle diameter of the aggregated particles is measured by a Coulter counter (trade name: TAII, manufactured by Nikkaki Bios Co., Ltd.), and the volume average particle diameter is 5.8 µm, and volume average particle size distribution (GSD) is 1.24.

3 parts of an anionic surfactant (trade name: NEOGEN R, manufactured by Dai-ichi Kogyo Seiyaku Co., Ltd.) is added to the aggregated particle dispersion to stop the aggregation, and the aggregated particles are stabilized. Thereafter, the stainless steel flask is sealed, and the content in the flask is heated to 97° C. with stirring by a magnetic seal, and heated for 3 hours, thereby the aggregated particles are coalesced. The volume average particle diameter of the coalesced particles is measured by a Coulter counter (trade name: TAII, manufactured by Nikkaki Bios Co., Ltd.), the volume average particle diameter is 6.3 µm, and volume average particle size distribution (GSD) is 1.24. The zeta potential of the particles is about 100 mV.

(Treatment of Fine Particles)

The aggregated particle dispersion prepared in the above-mentioned manner is a fine particle dispersion having a solid component concentration about 19% by volume. The fine particle dispersion fluid 1a obtained in the above-mentioned manner is set in a micro-syringe 31 provided with a syringe pump P1 of the treatment apparatus shown in FIG. 3 and introduced at a constant flow rate into the introduction section 2 of a microreactor 32.

Figure 3:
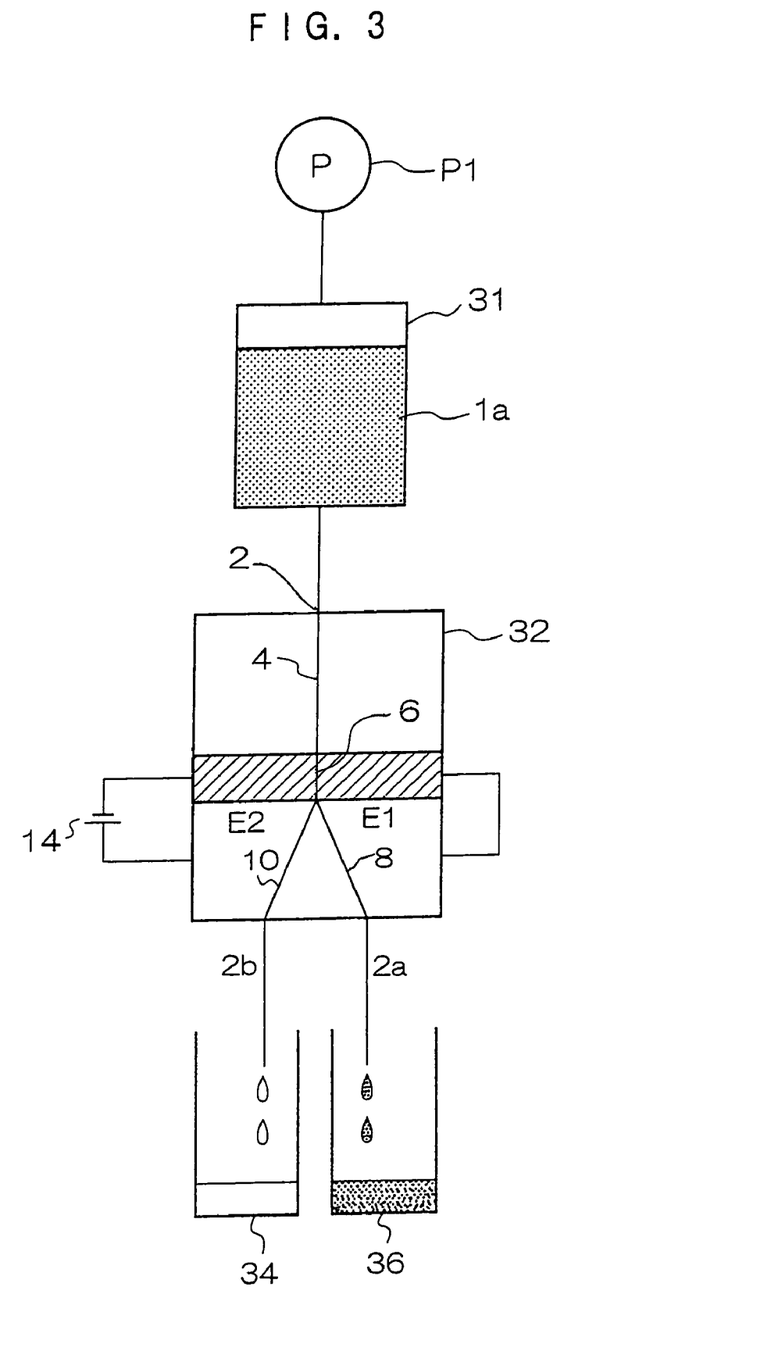
FIG. 3 is a schematic structural view showing one example of a concentration apparatus of a fine particle dispersion of the invention.

The width of the transporting section 4, recovery section 8, discharge section 10 and fine particle delivering section 6 in the microreactor 32 is 500 µm, respectively and the depth is 100 µm. The length of the transporting section 4 is set to 3 cm and the length of the fine particle delivering section 6 is set to 1 cm. The flow rate of the fine particle dispersion fluid 1a (the liquid transporting speed) in the transporting section 4 is set to 4.8 ml/hr and about 2V of the electric field is applied to the electrodes E1 and E2 connected to the electric power source 14. As a result, a liquid 2b which does not contain fine particles is discharged from an end outlet of the discharge section 10 and collected in a vessel 34. On the other hand, a fine particle dispersion 2a containing concentrated fine particles is discharged from an end outlet of the recovery section 8 and collected in a vessel 36. The content of the fine particles of the recovered fine particle dispersion 2a containing concentrated fine particles is about 47% by volume and the fine particles are concentrated to about 2.5 times. Although the liquid supply is continued for about 5 hours, no blocking nor clogging takes place and the recovery ratio of the fine particles is almost 100%.

Next, the production method of the microreactor 32 used in this case will be described.

Figure 4A:
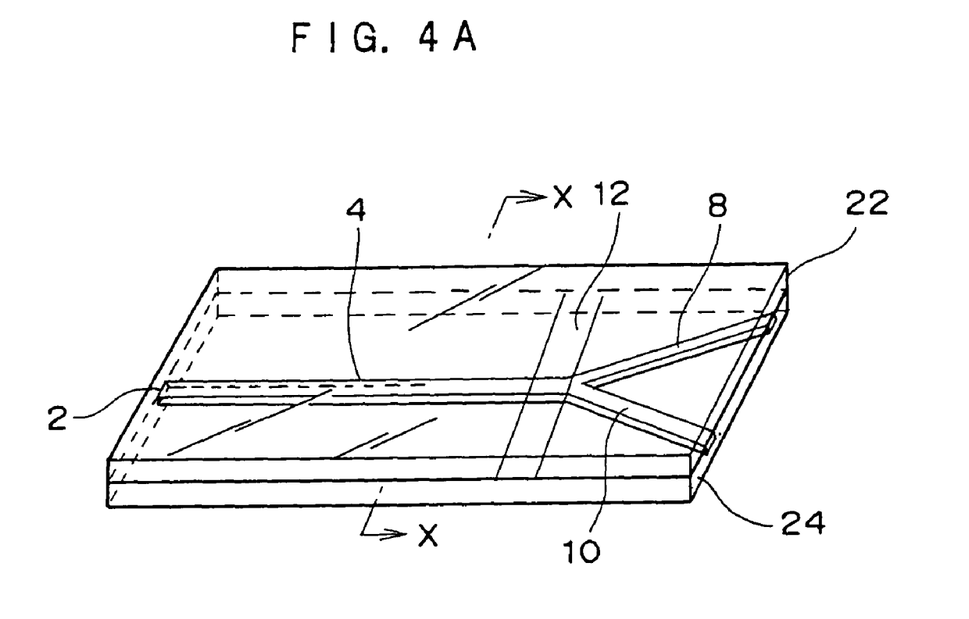
FIG. 4A is a perspective view showing the state that the PDMS chip and the glass substrate are stuck to each other.
Figure 4B:
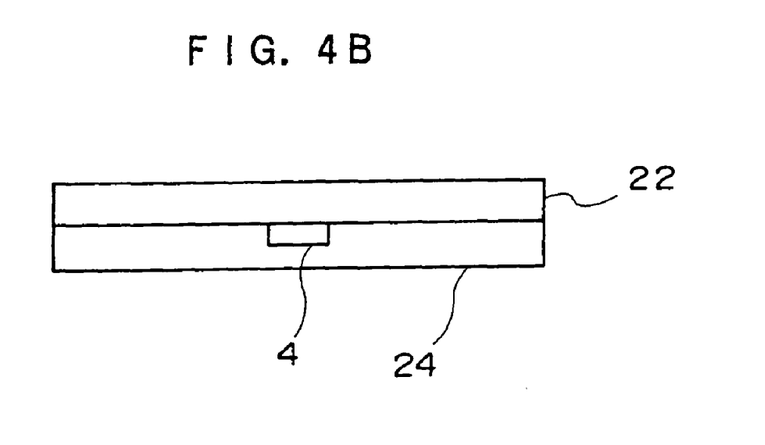
FIG. 4B is a schematic cross-sectional view along the X-X direction in state that the PDMS chip and the glass substrate are stuck to each other.

After Photoresist Su-8 (trade name: manufactured by Microchem Corp.) is applied to an Si substrate by a spin coater 1H-DX 2 (trade name: manufactured by Mikasa Co., Ltd.), using a mask previously prepared, patterning is carried out by a mask aligner MA-20 (trade name: manufactured by Mikasa Co., Ltd.) to obtain a mold. PDMA (polydimethylsiloxane: manufactured by Shin-Etsu Silicone Co., Ltd.) is poured to the mold and cured, and released from the mold to obtain a chip 24 made of PDMS having a recessed part at the center thereof. On the other hand, portions other than the portions in the channel side of a glass substrate where electrodes are to be formed are masked by a conventional method and platinum is deposited for about 15 minutes by a sputtering apparatus (trade name: HITACH E-1010) to form electrodes of about 90 nm. The above-PDMS chip 24 and the glass substrate 22 having the electrodes are laminated as shown in FIG. 4 to obtain a micro-device (microreactor 32).

The liquid transporting section of the thus obtained microreactor 32 has an angle of about 0° relative to the gravity direction, a cross sectional shape is a rectangular shape of which the length in the direction perpendicular to the flow in the channel (hereinafter, referred to as depth direction) is 100 µm and the length in the direction parallel to the electric field direction (hereinafter, referred to as lateral direction) is 500 µm and a length of the channel is 3 cm. A fine particle delivering section 6 is located at the downstream side of the transporting section 4 and has the same cross section as that of the transporting section 4 and a length of about 1 cm, and the electric field is applied to the delivering section by the electrode parts E1 and E2. The microreactor also has a recovery section 8, which locates at the downstream side of the fine particle delivering section 6 and the positive side of the electrodes, and has an angle of about 30° relative to the gravity direction, and has a rectangular shape which has a length of 100 µm in the depth direction, a length of 175 µm in a direction parallel to the electric field (hereinafter referred to as lateral direction), and a length of 3 cm. The microreactor further has a discharge section 10, which locates at the opposite side of the recovery section 8, and has an angle of about 30° relative to the gravity direction, and has a rectangular shape which has a length of 100 µm in the depth direction a length of 260 µm in the lateral direction, and a length of 3 cm.

According to the present invention, a concentration method of a fine particle dispersion containing fine particles to be electrophoretically migrated for concentrating the dispersion at a low energy and a high efficiency and a high fine particle recovery efficiency in a short time period can be provided and a compact type and space-saving concentration apparatus of a fine particle dispersion containing fine particles to be electrophoretically migrated for concentrating the dispersion at a low energy and a high efficiency and a high fine particle recovery efficiency in a short time period can be provided.

What is claimed is:

1. A concentration method of a fine particle dispersion, the method comprising:
    making the fine particle dispersion flow in a laminar flow to a channel having micro-width and an angle in the range of 0 to 45° with respect to the gravity direction or the buoyant direction, the fine particle dispersion comprising fine particles having zeta potential;
    applying a direct current electric field in a direction intersecting the flowing direction of the fine particle dispersion so that the fine particles electrophoretically migrate to one direction of the electric field; and
    discharging a liquid other than the fine particle dispersion.

2. The concentration method of a fine particle dispersion according to claim 1, wherein the channel having a micro-width has a width of 50 to 1,000 µm.

3. The concentration method of a fine particle dispersion according to claim 1, wherein the direct current electric field is applied to the channel at an angle in the range of 30 to 150° with respect to the direction of the fine particle dispersion flow in a fine particle transporting section.

4. The concentration method of a fine particle dispersion according to claim 1, wherein the flow rate of the fine particle dispersion in a liquid delivering section is in the range of 0.001 to 100 ml/hr.

5. The concentration method of a fine particle dispersion according to claim 1, wherein the fine particles to be electrophoretically migrated have absolute value of zeta potential in the range of 1 to 1,000 mV.

6. The concentration method of a fine particle dispersion according to claim 1, wherein the fine particles have a volume average particle diameter in the range of 0.1 µm to 500 µm.

7. The concentration method of a fine particle dispersion according to claim 1, wherein a liquid medium in the fine particle dispersion has a conductivity in the range of 0 to 50 µs/cm.

8. The concentration method of a fine particle dispersion according to claim 1, wherein the difference calculated by subtracting the specific gravity of the liquid medium of the fine particle dispersion from the specific gravity of the fine particles is in the range of −0.9 to 20.

9. The concentration method of a fine particle dispersion according to claim 1, wherein the concentration of the fine particles in the fine particle dispersion is in the range of 0.1 to 40% by volume.

* * * * *